United States Patent
Wang et al.

(10) Patent No.: US 7,411,176 B2
(45) Date of Patent: Aug. 12, 2008

(54) METHOD AND APPARATUS FOR EXAMINING CORROSION OF TENDON EMBEDDED IN CONCRETE

(75) Inventors: Chung-Yue Wang, Taipei (TW); Peng-Ching Peng, Zhonghe (TW)

(73) Assignee: National Central University, Taoyuan (TW)

( * ) Notice: Subject to any disclaimer, the term of this patent is extended or adjusted under 35 U.S.C. 154(b) by 612 days.

(21) Appl. No.: 11/041,963

(22) Filed: Jan. 26, 2005

(65) Prior Publication Data

US 2006/0176929 A1 Aug. 10, 2006

(51) Int. Cl.
 *G01J 1/04* (2006.01)
(52) U.S. Cl. .................. 250/227.14; 250/227.15; 250/227.16; 250/227.18; 385/12
(58) Field of Classification Search ............ 250/227.18, 250/227.16, 227.15, 227.14, 227.11; 385/13, 385/12
See application file for complete search history.

(56) References Cited

U.S. PATENT DOCUMENTS

| | | | | |
|---|---|---|---|---|
| 4,996,884 A | * | 3/1991 | Lessing | 73/800 |
| 5,493,390 A | * | 2/1996 | Varasi et al. | 356/32 |
| 5,646,400 A | * | 7/1997 | Perez et al. | 250/227.18 |
| 6,047,094 A | * | 4/2000 | Kalamkarov et al. | 385/12 |
| 6,191,414 B1 | * | 2/2001 | Ogle et al. | 250/227.14 |
| 6,384,404 B1 | * | 5/2002 | Berg | 250/227.16 |
| 6,600,149 B2 | * | 7/2003 | Schulz et al. | 250/227.14 |
| 6,610,399 B1 | * | 8/2003 | Crigler | 428/375 |
| 6,949,933 B2 | * | 9/2005 | Weaver | 324/541 |
| 7,138,621 B2 | * | 11/2006 | Wang | 250/227.14 |
| 2006/0049341 A1 | * | 3/2006 | Wang et al. | 250/227.14 |
| 2006/0176929 A1 | * | 8/2006 | Wang et al. | 374/45 |

* cited by examiner

*Primary Examiner*—John R Lee
(74) *Attorney, Agent, or Firm*—Troxell Law Office, PLLC

(57) ABSTRACT

The present invention measures the strain caused by the shrink and expansion from the corrosion and examines the corrosion of a tendon for a long term with high sensitivity to improve the accuracy of the examination.

24 Claims, 5 Drawing Sheets

METHOD AND APPARATUS FOR EXAMINING CORROSION OF TENDON EMBEDDED IN CONCRETE

FIELD OF THE INVENTION

The present invention relates to corrosion examination; more particularly, relates to examining the corrosion of a tendon for a long term with high sensitivity to improve the accuracy of the examination.

DESCRIPTION OF THE RELATED ARTS

A common prestressed concrete construction is widely applied to a bridge, a building, a flood gulf, an irrigation work, a road, etc. When the concrete bears load, a stress and a strain is happened to the material of the structure. And, when the stress or the strain exceeds an allowance, the material will be broken to be destroyed. So, if a force opposite to the load can be directed to the material, the stress on the sectional surface can be lessened and be controlled under the allowance. The force directed to the structure here is called a prestress and the producing of the prestress can be done in a physical or mechanical way.

The physical and mechanical methods are to apply a force to one of two materials to produce a pressure on that one material; and the chemical method is to produce a force by a chemical change. Among prestressing methods, the mechanical method is used most often that the prestress is fixed at a beam end by a specific prestressing machine and a fixing facility. The mechanical method is a well-known prestressing method.

The general high-tensile tendons used in prestressed concrete are made with steel wires, steel rods or twisted steel ropes. Because the length and the number the steel wire is adjustable, it is usually used in pre-pull or post-pull method while the diameter of the steel wire can be wide and varied from 2 mmφ to 8 mmφ. Since its adhesion force does not fully meet the requirements recently, the pre-pulled prestress beam starts to be made with twisted steel ropes more than with steel wires.

Besides, the fixing method for the steel wire has a certain consideration on the prestress loss caused by the sliding of the steel wire. And, the reserved steel wire for applying force can be a waste and so cost more. Concerning anchoring devices, the anchoring device for the twisted steel rope is the most expansive; that for the steel wire follows; and that for the steel rod is the cheapest. When using the twisted steel rope, the item of the anchoring device for a long-span beam takes a smaller part of the expenses than that for a short-span one. When using the steel rod, its anchoring device is cheaper, but its stress is smaller and its length is shorter, which needs bar couplers to prolong its length to be used in a long-span beam and so becomes expensive under this situation.

When the pre-pulled prestress beam is used in a short-span beam, its cost is low owing to the savings from the anchoring device, bushing and grouting. But, if the cast beam factory is quite far from the construction site, it is not easy to move the beam.

A bridge built with a Preflexed Steel Girder is using a prestress: an I-beam of steel is pre-deformed at the opposite direction to the to-be-borne load to obtain force; the beam is wrapped by a concrete at the pulling part; and the force previously added on the beam is removed as the concrete is solidified so that the force is transferred to the concrete.

No matter how the tendon is made, when the pulling force is too big at the free end of the tendon or the tendon is used for a long time, a plastic yield fracture will be apt to happen to the tendon. Because the prestress of the tendon with a high degree of intensity is suddenly released, the tendon will be strongly sprung to be ejected which is apt to hurt people and machines. So, it is required for the prestressed tendon to have a monitoring device with high sensitivity for a long term monitoring so that the trend of the corrosion of the tendon can be examined.

SUMMARY OF THE INVENTION

Therefore, the main purpose of the present invention is to be widely applied to examining the corrosion of a tendon for a long term; and, to measure the corrosion trend of the tendon to evaluate the safety of a structure.

Another purpose of the present invention is to examine the corrosion of a tendon for a long term with high sensitivity to improve the accuracy of the examination Still another purpose of the present invention is to obtain the strength of the tendon by analyzing a reflection wavelength as a reference for strengthening the structure.

To achieve the above purposes, the present invention is a method and an apparatus for examining corrosion of a tendon embedded in a concrete. The apparatus comprises a tendon of twisted pairs of steel wire strands with a gap between every two neighboring strands; at least one sensor connected to a coupler with a proper protection and set in the gap between the steel wire strands; a laser connected with the coupler; and an analyzer connected with the coupler. The at least one sensor can be set between every two neighboring steel wire strands in the tendon; a light source is transmitted by the laser through the coupler to the sensor; the light source is passed through the sensor and is returned to the analyzer; and, in the end, the wavelength drift of the light source, related to the strain, is examined by the analyzer to obtain the strain of the tendon caused by the shrink and expansion from the corrosion. Accordingly, a method and an apparatus for examining the corrosion of a tendon embedded in a concrete are obtained.

BRIEF DESCRIPTIONS OF THE DRAWINGS

The present invention will be better understood from the following detailed descriptions of the preferred embodiment according to the present invention, taken in conjunction with the accompanying drawings, in which FIG. 1 is a view of a system according to the present invention;

DESCRIPTION OF THE PREFERRED EMBODIMENT

Figure 1:
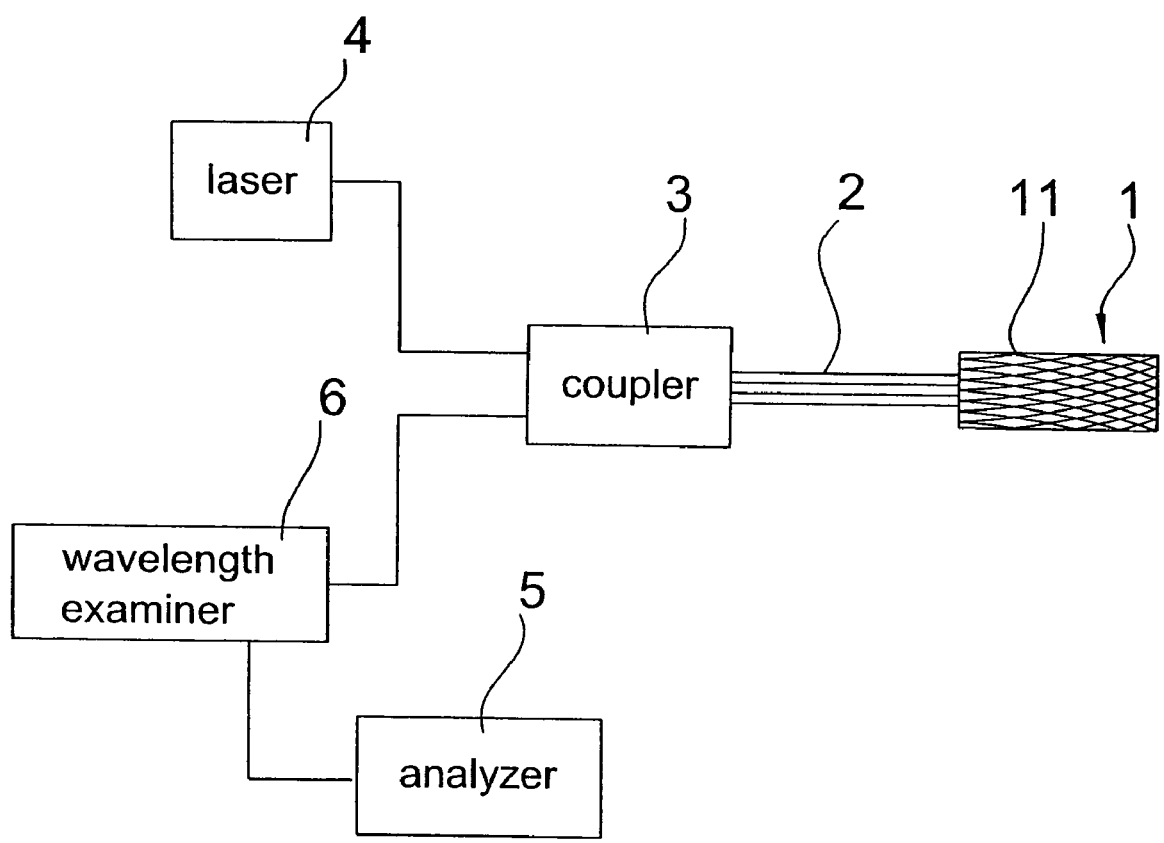

The following description of the preferred embodiment is provided to understand the features and the structures of the present invention.

Please refer to FIG. 1 through FIG. 5, which are a view of a system, views of two statuses of use, a view of a functional diagram, and a view of still another status of use, according to the present invention. As shown in the figures, the present invention is a method and an apparatus for examining corrosion of a tendon embedded in a concrete. The apparatus comprises a tendon 1, at least a sensor 2, a coupler 3, a laser 4 and an analyzer 5.

The tendon 1 comprises a plurality of twisted pairs of steel wire strands 11 and a gap 12 between each two neighboring steel wire strands 11 respectively.

A fiber Bragg grating 21 is set at the sensor 2. The sensor 2 is connected to a coupler with a proper protection. The sensor can be a cylinder bushing or can be deposed in a cylinder bushing.

The laser 4 is connected with the coupler 3; a light is transmitted by the laser to the sensor 2 through the coupler 3; and the laser 4 is a broadband source capable of transmitting a broadband light.

The analyzer 5 is connected with the coupler 3; the analyzer 5 is used to receive the light source returned through the sensor 2; the analyzer 5 can be a spectrum analyzer or a power meter so that, by the help of the coordination of the analyzer 5 and a wavelength examiner for re-confirming, the accuracy of the examination can be greatly improved; and the wavelength examiner can be set between the coupler 3 and the analyzer 6.

Figure 2:
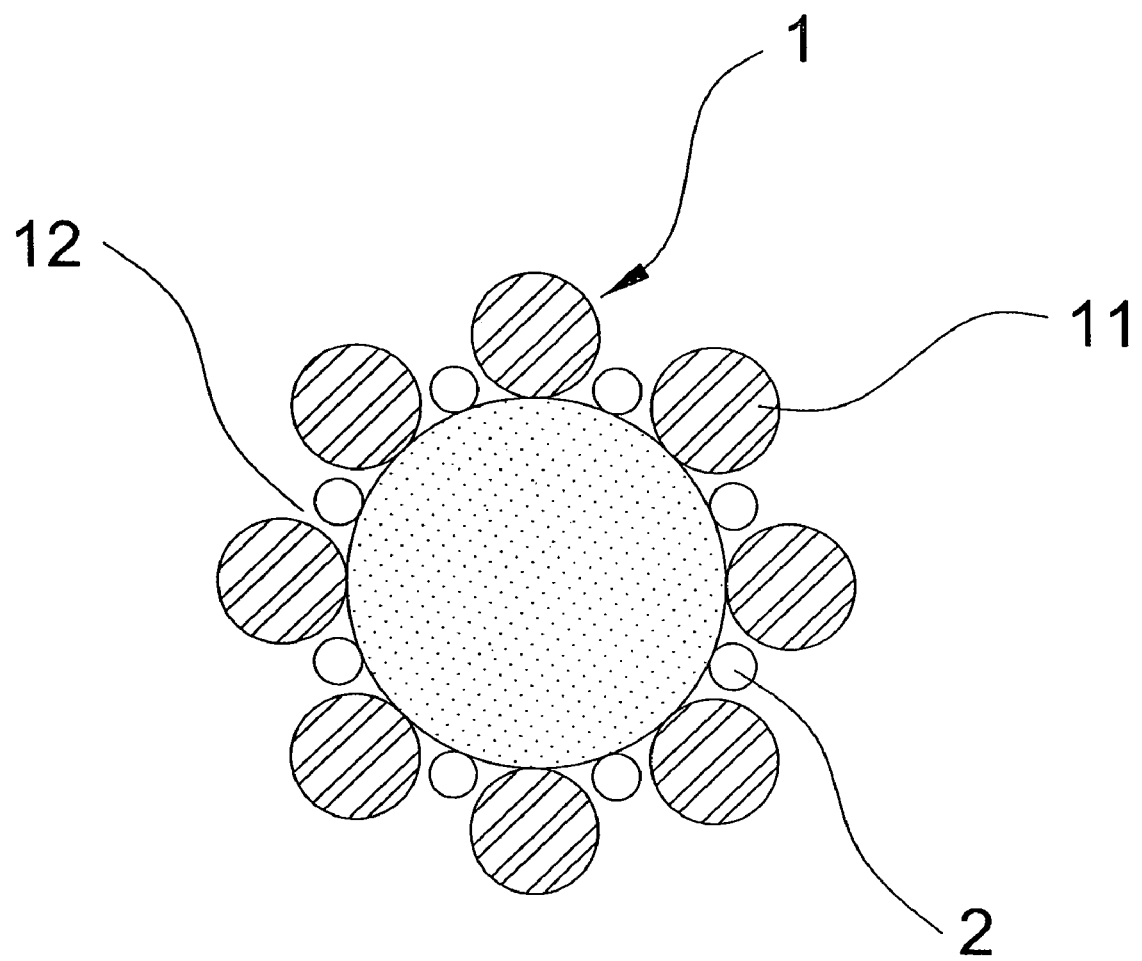
FIG. 2 is a view of a status of use according to the present invention.
Figure 3:
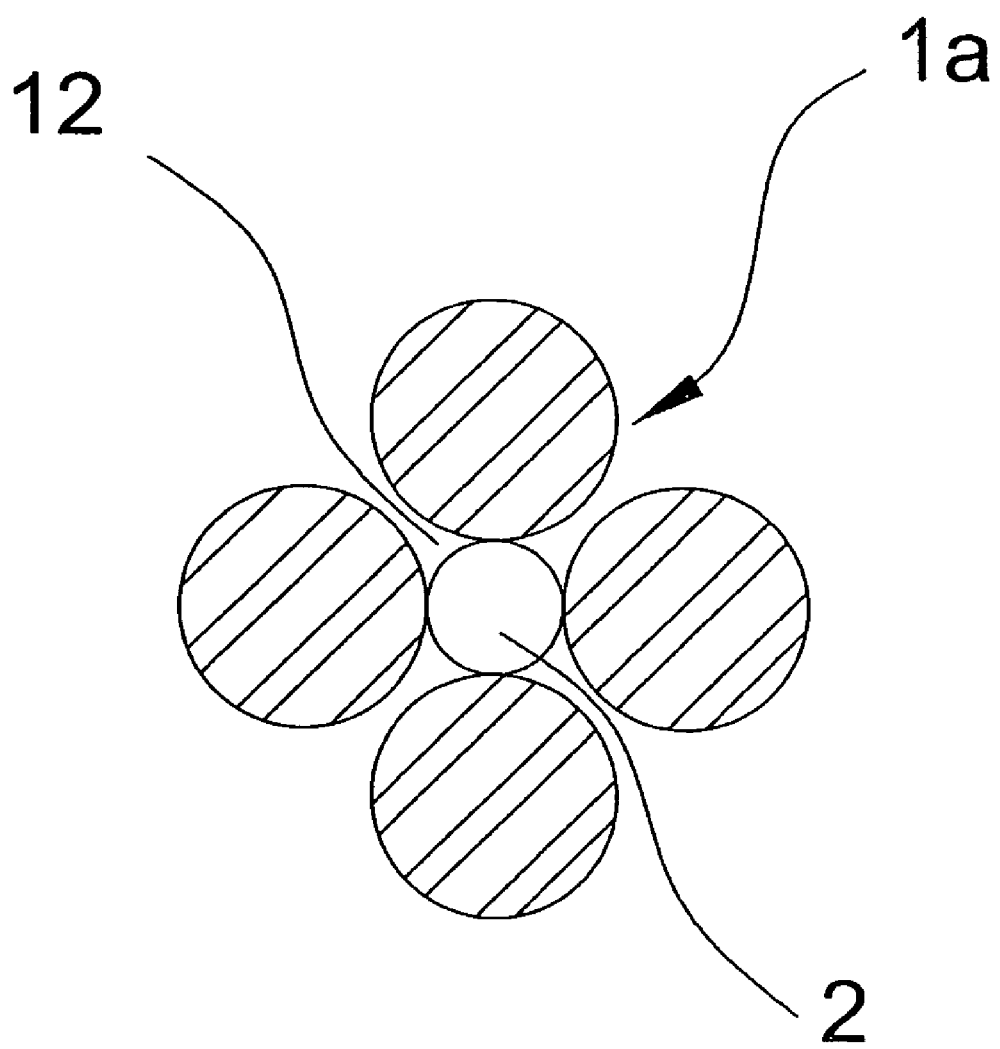
FIG. 3 is a view of another status of use according to the present invention.
Figure 4:
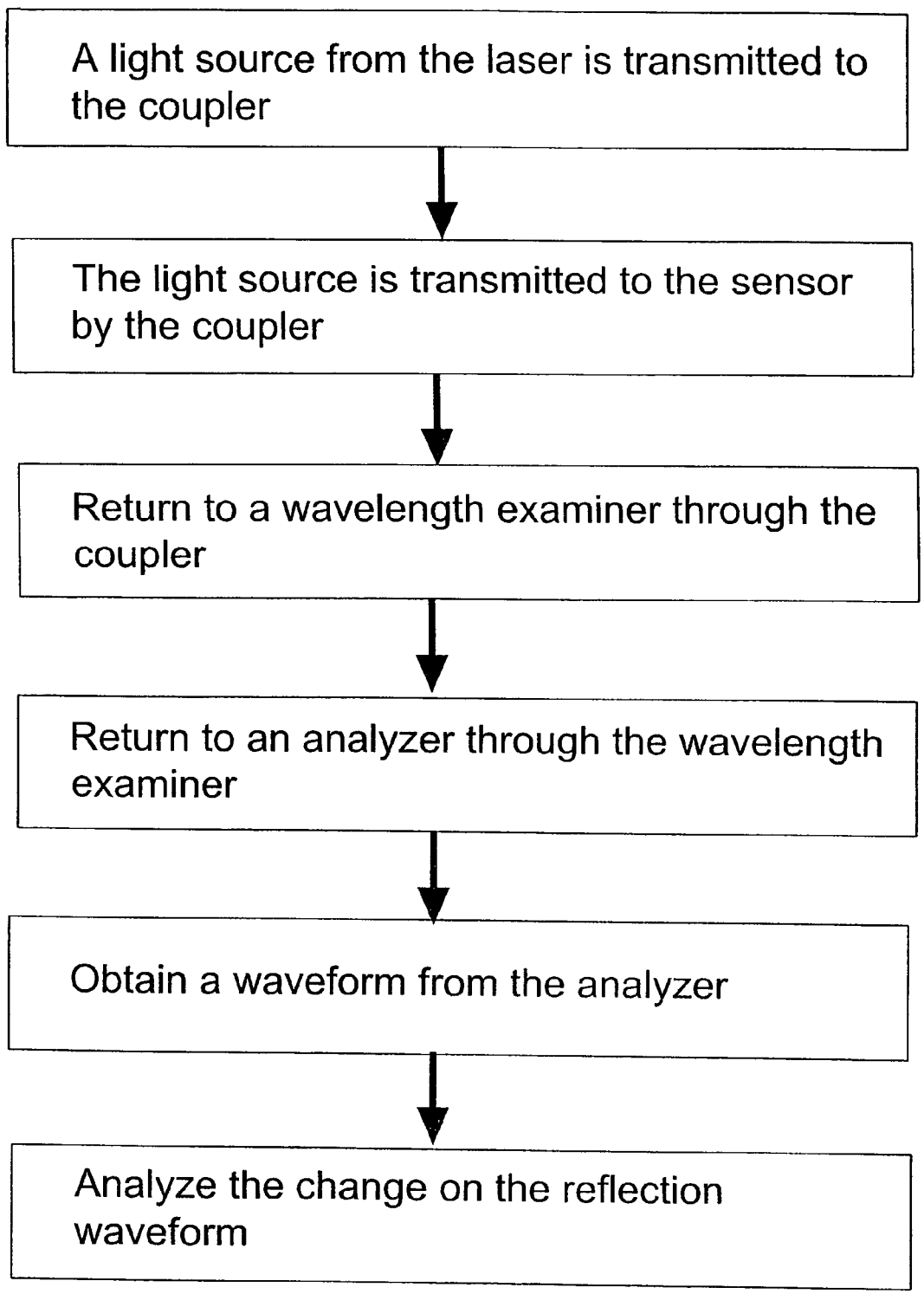
FIG. 4 is a view of a functional diagram according to the present invention.
Figure 5:
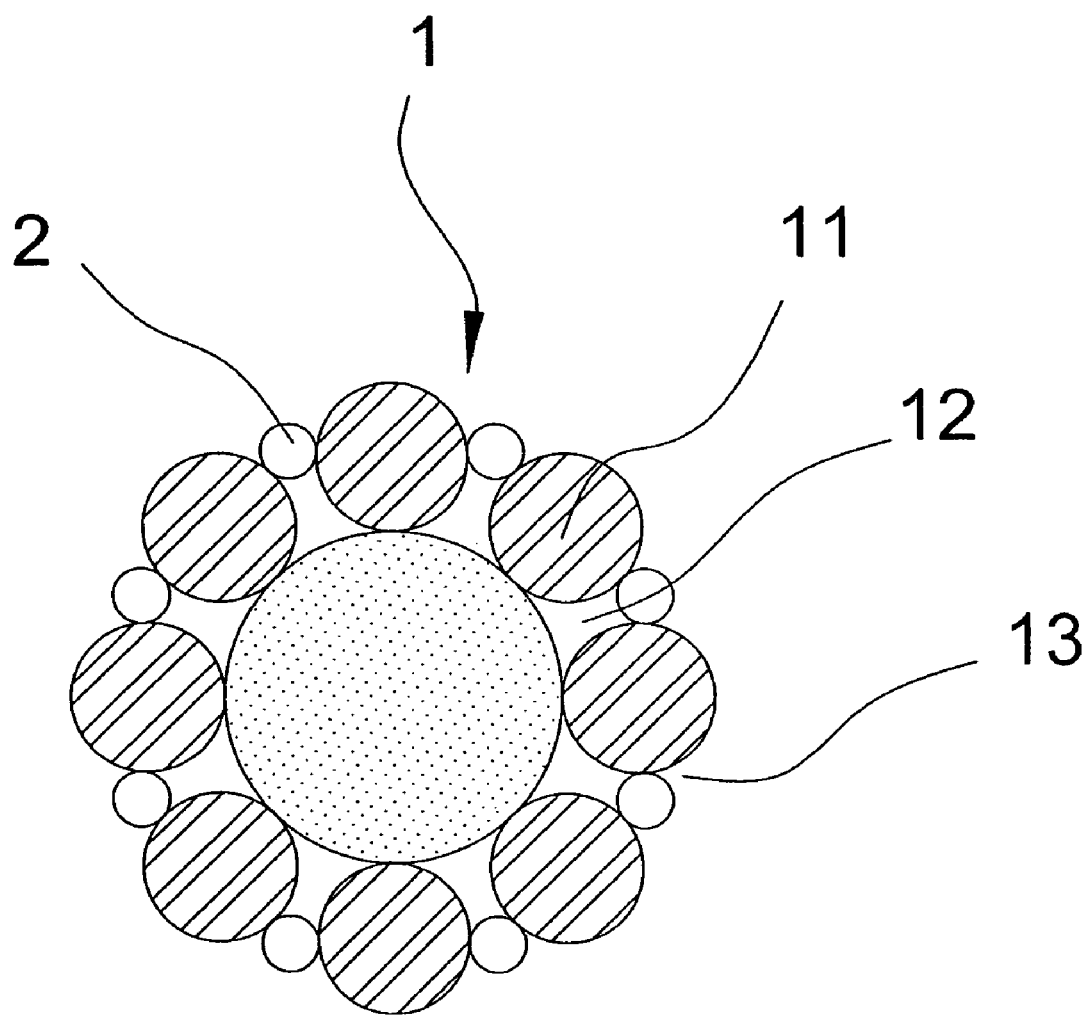
FIG. 5 is a view of still another status of use according to the present invention.

When using the present invention, the sensor 2 can be set at the bottom of the gap 12 between every two neighboring steel wire strands 11 (as shown in FIG. 2), or can be set at the top edge of the gap 12 between every two neighboring steel wire strands 11 with an adhesive 13 of a gum (as shown in FIG. 5). The tendon 1,1a can be of different types (as shown in FIG. 2 and FIG. 3). The analyzer 5 can be set in a control room (such as a machine room or a guard room) so that the corrosion of the tendon can be monitored or examined for a long term as a reference to judge the safety of the structure in the future.

When examining, a broadband light is transmitted from a broadband source of the laser 4. The broadband source is then transmitted through the coupler 3 to the sensor 2. At the moment, the light source transmitted to the sensor 2 from the laser 4 is reflexed back to the analyzer 5 by the wavelength examiner 6 between the coupler 3 and the analyzer 5 to obtain a reflection waveform. The reflection waveform is then examined by the sensor 2 to obtain the change in the curve rate caused by the shrink and expansion from the corrosion, which produces the difference in the power loss rate of the light. The fiber Bragg grating 21 at the sensor typically comprises a fixed waveform. When the tendon is deformed by the shrink and expansion from the corrosion, the waveform of the fiber Bragg grating 21 will be changed. Therefore, if there is no shift with the waveform of the fiber Bragg grating 21, the tendon is not deformed; otherwise, the tendon is deformed by the shrink and expansion from the corrosion. Besides, because the reflection wavelength of the sensor 2 corresponds the strain on the sensor 2, by setting the fiber Bragg grating 21 at the sensor 2, the strain caused by the shrink and expansion from the corrosion can be measured so that the deformation of the tendon caused by the shrink and expansion from the corrosion can be managed through examining for a long term the change in reflection wavelength.

To sum up, the present invention is a method and an apparatus for examining corrosion of a tendon embedded in a concrete, which surmount the difficulties on examining the corrosion of a tendon. The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. An apparatus for examining corrosion of a tendon embedded in concrete, comprising:
   a tendon comprising a plurality of twisted pairs of steel wire strands while having a gap between every two neighboring steel wire strands;
   at least a sensor deposed in said gap respectively and connected to a coupler;
   a laser connected with said coupler, by which a light signal is transmitted through said coupler to said sensor; and
   an analyzer connected with said coupler, into which said light signal is received to be measured and analyzed after said light signal is returned from passing through said sensor.

2. The apparatus for examining corrosion of a tendon embedded in the concrete according to claim 1, wherein said sensor comprises a fiber Bragg grating.

3. The apparatus for examining corrosion of a tendon embedded in the concrete according to claim 1, wherein said sensor is a cylinder bushing.

4. The apparatus for examining corrosion of a tendon embedded in the concrete according to claim 1, wherein said sensor is deposed in a cylinder bushing.

5. The apparatus for examining corrosion of a tendon embedded in the concrete according to claim 1, wherein said sensor is deposed at a bottom of said gap.

6. The apparatus for examining corrosion of a tendon embedded in the concrete according to claim 1, wherein said sensor is deposed at and adhered to a top edge of said gap with an adhesive.

7. The apparatus for examining corrosion of a tendon embedded in the concrete according to claim 6, wherein said adhesive is a gum.

8. The apparatus for examining corrosion of a tendon embedded in the concrete according to claim 1, wherein said coupler is a one-to-two coupler.

9. The apparatus for examining corrosion of a tendon embedded in the concrete according to claim 1, wherein said laser is a broadband source transmitting a broadband light.

10. The apparatus for examining corrosion of a tendon embedded in the concrete according to claim 1, wherein said analyzer is a spectrum analyzer.

11. The apparatus for examining corrosion of a tendon embedded in the concrete according to claim 1, wherein said analyzer is a power meter.

12. The apparatus for examining corrosion of a tendon embedded in the concrete according to claim 1, wherein a wavelength analyzer is deposed between said coupler and said analyzer.

13. A method for examining corrosion of a tendon embedded in concrete, comprising:
   step a: obtaining at least a sensor to be connected to a coupler, and deposing said sensor respectively in a gap between every two neighboring steel wire strands of said tendon; and
   step b: connecting a laser and an analyzer to said coupler, wherein a light signal is transmitted by said laser to said sensor through said coupler,
   wherein said light signal is returned to said analyzer through said sensor, and
   wherein a wavelength drift of said light signal is detected by said analyzer to obtain a strain of said tendon caused by shrink and expansion of said tendon.

14. The method for examining corrosion of a tendon embedded in the concrete according to claim 13, wherein a fiber Bragg grating is deposed at said sensor.

15. The method for examining corrosion of a tendon embedded in the concrete according to claim 13, wherein said sensor is a cylinder bushing.

16. The method for examining corrosion of a tendon embedded in the concrete according to claim 13, wherein said sensor is deposed in a cylinder bushing.

17. The method for examining corrosion of a tendon embedded in the concrete according to claim 13, wherein said sensor is deposed at a bottom of said gap.

18. The method for examining corrosion of a tendon embedded in the concrete according to claim 13, wherein said sensor is deposed at and adhered to a top of said gap with an adhesive.

19. The method for examining corrosion of a tendon embedded in the concrete according to claim 18, wherein said adhesive is a gum.

20. The method for examining corrosion of a tendon embedded in the concrete according to claim 13, wherein said coupler is a one-to-two coupler.

21. The method for examining corrosion of a tendon embedded in the concrete according to claim 13, wherein said laser is a broadband source transmitting a broadband light.

22. The method for examining corrosion of a tendon embedded in the concrete according to claim 13, wherein said analyzer is a spectrum analyzer.

23. The method for examining corrosion of a tendon embedded in the concrete according to claim 13, wherein said analyzer is a power meter.

24. The method for examining corrosion of a tendon embedded in the concrete according to claim 13, wherein a wavelength examiner is deposed between said coupler and said analyzer.

* * * * *